United States Patent [19]

Fiala

[11] Patent Number: Plant 7,492

[45] Date of Patent: Apr. 9, 1991

[54] FLOWERING CRAB APPLE TREE 'SINAI FIRE'

[75] Inventor: John L. Fiala, Medina, Ohio

[73] Assignee: J. Frank Schmidt & Son Co., Boring, Oreg.

[21] Appl. No.: 351,870

[22] Filed: May 12, 1989

[51] Int. Cl.[5] ..... A01H 5/00

[52] U.S. Cl. ..... Plt./34

[58] Field of Search ..... Plt./34

*Primary Examiner*—James R. Feyrer

*Attorney, Agent, or Firm*—Klarquist, Sparkman, Campbell, Leigh & Whinston

[57] ABSTRACT

A new variety of crab apple tree, which I call 'Sinai Fire', has white flowers, weeping branches and red fruit. The new variety is resistant to apple scab.

1 Drawing Sheet

DESCRIPTION

The present invention relates to a new and distinct variety of flowering crab apple tree which I have named Sinai Fire.

My new variety originated out of a breeding program as a cross of Malus 'Red Swan'×Malus 'Amberina', both of which are cultivars I discovered as a result of earlier hybridizing efforts. My attention was first directed to this plant because of its thick, glossy large leaves and weeping form. Further observation over time showed that this plant had a high degree of resistance to apple scab. In comparison, most other crab apple trees are moderately or severely susceptible to apple scab. In addition, the flowers of my new variety are white and my new variety has small, intensely colored, orange-red fruit.

I observed my new variety for a number of years growing in a cultivated area on my Falconskeape farm in Medina, Ohio. My observations have confirmed that my variety is distinct and unusual cultivar. Subsequent asexual propagation of my variety by budding under my direction at the nursery of J. Frank Schmidt & Son Co. in Boring, Oreg., and observation of the resulting progeny has proven the characteristics of my new variety to be fixed. Furthermore, these observations have confirmed that my new variety represents a new and improved variety of flowering crab apple tree, as particularly evidenced by the following unique combination of characteristics, which have proven firmly fixed, are outstanding therein, and which distinguish it from all other varieties of this species of which I am aware:

1. Weeping branches;
2. Thick glossy green leaves;
3. White flowers and red fruit; and
4. High resistance to apple scab.

The accompanying photographs depict the color of the leaves and fruit of my variety, as well as the shape of the tree, as nearly true as is reasonably possible to make the same in a color illustration of this character.

FIG. 1 is a color photograph of a tree of the present invention generally showing the weeping form of its branches;

FIG. 2 is a color photograph of flowers and leaves of the tree of the present invention; and FIG. 3 is a color photograph of fruit and leaves of the tree of the present invention.

My new Malus 'Sinai Fire' variety differs from its two parent cultivars in the following manner:

Malus 'Amberina' is an upright growing, rounded tree while my 'Sinai Fire' variety has a weeping habit.

Malus 'Red Swan' does have a weeping growth habit, however, it differs from my new variety in that it has elongated, oval fruit which is broader at the stem end than the calyx end. In contrast, my 'Sinai Fire' variety has round fruit. In addition, the 'Red Swan' variety has narrower leaves which end in a long acuminate tip, while the leaf tips of 'Sinai Fire' are acute.

The following comparison chart shows how my new variety of tree differs in some respects from other flowering crab apple cultivars having a weeping growth form and pinkish white flowers:

| Cultivar | Feature | Characteristics of Cited Cultivar |
|---|---|---|
| Ann E | Leaf | 2.0–3.0 × 5.0–7.0 cm. |
| (Manbeck Weeper) | Scab resistance | Poor to moderate |
| | Leaf surface | Dull |
| Blanche Ames | Flower | Semi Double or double |
| | Fruit | Yellow |
| Elise Rathke | Fruit | Greenish Yellow |
| | | 3.5–5.0 cm |
| Louisa | Flower | Pink |
| | Fruit | Yellow |
| Red Jade | Leaf | 2.0–4.5 c.m. × 5.0–7.5 cm. |
| | Scab resistance | Poor |
| | Leaf surface | Slightly glossy |
| Thiel | Flower | Pink or pinkish white |
| (Exzellenz | Fruit | 1.8 cm. or larger |
| Thiel) | | Angular |
| White Cascade | Flower | 2.0–2.5 cm. |
| | Fruit | Yellow |

| Cultivar | Characteristics of My New Variety |
|---|---|
| Ann E | 3.0–5.0 × 7.0–9.0 cm. |
| (Manbeck Weeper) | Very good |
| | Very glossy |
| Blanche Ames | Single |
| | Red |
| Elise Rathke | Red |
| | 1.0–1.3 cm. |
| Louisa | White |
| | Red |
| Red Jade | 3.0–5.0 × 7.0–9.0 cm. |
| | Very good |
| | Very glossy |
| Thiel | White |
| (Exzellenz | 1.0–1.3 cm. |
| Thiel) | Round |
| White Cascade | 3.0–3.5 cm. |
| | Red |

The following is a detailed description of my new variety of Malus 'Sinai Fire' flowering crab apple tree, with color terminology in accordance with the Royal Horticultural Society Colour Chart (hereinafter RHS), published by the Royal Horticultural Society of London.

Parentage: Malus 'Red Swan'×Malus 'Amberina'.

Propagation: Holds to distinguishing characteristics through succeeding propagation by budding.

Locality where grown and observed: Medina, Ohio and Boring, Oreg.

Tree: Branches weeping from a generally upright main trunk.

Vigor: Moderately vigorous, being slightly above average in vigor among commercial crab apple cultivars. In the Northwest Oregon locale, one year old budded trees have been observed to grow to 1.6 meters while other crab apple cultivars have been observed to grow one to two meters as one year budded plants.

Growth rate: Six year old trees growing in Northwest Oregon have been observed to be 3.5 meters in height and are half of estimated mature height. At this stage, terminal growth elongation averages 45 cm. per year.

Foliage:

*Size.*—7.0–9.0 cm long×3.0–5.0 cm wide.

*Shape.*—Ovate.

*Apex.*—Acute.

*Base.*—Broadly wedge-shaped.

*Margin.*—Serrate.

*Color.*—RHS Green 141B to 143A, glossy.

Buds: RHS Red 50C.

Blooms: Annually.

*Character.*—Single, opening very flat.

*Size.*—3.0–4.0 cm. diameter.

*Color.*—White RHS 155DL.

*Count.*—Average flower count per spur 5.

Seed: Five per fruit, ovoid, 1.5 mm×1.0 mm, seed coat like RHS Brown 200A.

Fruit:

*Shape.*—Round.

*Size.*—1.0–1.3 cm. in diameter.

*Color.*—Red 44A to 45B.

*Count.*—Average fruit count per spur 4.5.

*Stem length.*—Average fruit stem length 27 mm.

*Retention.*—Fruit persists on tree until the first week in November in Northwest Oregon.

Ultimate tree size: Unknown at this time as original tree has not yet reached mature size. Based on growth rate and form, it is expected to mature at 6 to 7 meters in height and 4 to 5 meters in width.

Ultimate tree shape: Unknown at this time as the original tree has not yet reached maturity. Expected to be irregularly oval in shape with a strong central trunk and branches which spread stiffly horizontally from the trunk, then weep.

Bark: Moderately smooth for first 5 years, then developing shallow longitudinal fissures.

*Bark color.*—Similar to RHS Grey-Brown 199A or slightly darker. Lenticels are raised, like RHS Greyed Orange 164A.

Branching habit: Tree consists of a strongly upright central trunk with slender but mostly stiffly horizontal branches evolving from the main trunk with strong crotch angles of substantially ninety degrees. Scaffold branches are narrowly spaced along the trunk and weep with progressive length from their points of attachment.

Precocity: Average for a commercial cultivar. Blooms and fruits sparsely in second year and moderately in third year under Northwest Oregon growing conditions.

I claim:

1. A new and distinct variety of flowering crab apple tree substantially as herein shown and described, characterized particularly as to novelty by its weeping branches, glossy green leaves, white flowers and red fruit and high resistance to apple scab.

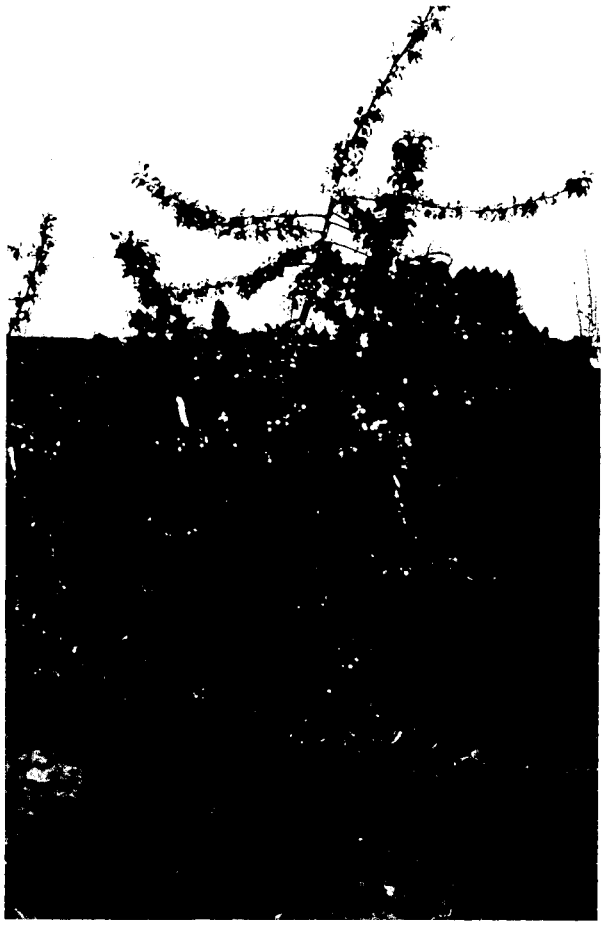
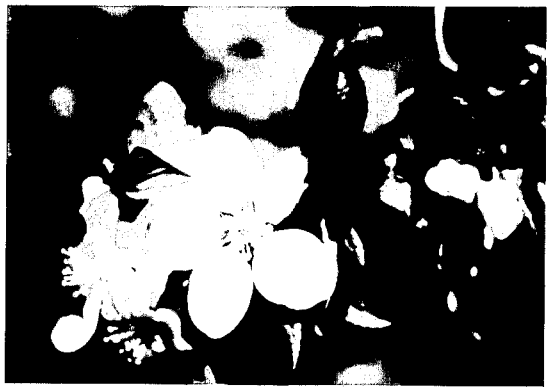
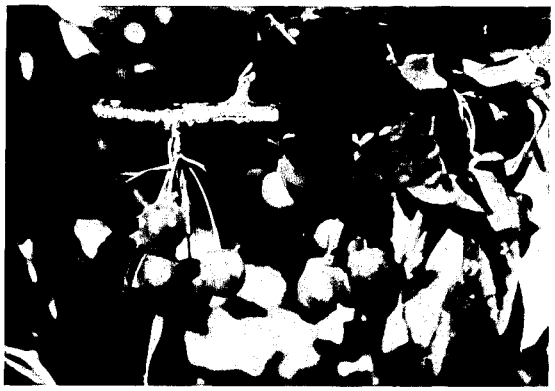

* * * * *